United States Patent
Benner et al.

(10) Patent No.: US 11,034,964 B1
(45) Date of Patent: *Jun. 15, 2021

(54) BINDING MOLECULES BUILT FROM L-DNA WITH ADDED NUCLEOTIDES

(71) Applicants: Steven A Benner, Gainesville, FL (US); Diane Rowold, Gainesville, FL (US)

(72) Inventors: Steven A Benner, Gainesville, FL (US); Diane Rowold, Gainesville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/719,232

(22) Filed: Dec. 18, 2019

Related U.S. Application Data

(63) Continuation of application No. 15/639,336, filed on Jun. 30, 2017, now Pat. No. 10,513,704, which is a continuation-in-part of application No. 14/082,800, filed on Nov. 18, 2013, now Pat. No. 9,725,713, which is a continuation-in-part of application No. 13/493,172, filed on Jun. 11, 2012, now Pat. No. 8,586,303, which is a continuation-in-part of application No. 12/999,138, filed on Dec. 15, 2010, now Pat. No. 8,614,072.

(51) Int. Cl.
*C12N 15/115* (2010.01)
*C12P 19/34* (2006.01)
*C12Q 1/6811* (2018.01)

(52) U.S. Cl.
CPC ............ *C12N 15/115* (2013.01); *C12P 19/34* (2013.01); *C12Q 1/6811* (2013.01); *C12N 2310/16* (2013.01); *C12N 2310/33* (2013.01)

(58) Field of Classification Search
CPC .............. C12N 15/115; C12N 2310/16; C12N 2310/33; C12P 19/34; C12Q 1/6811
See application file for complete search history.

(56) References Cited

U.S. PATENT DOCUMENTS 9,062,345 B1 * 6/2015 Benner ................. C12Q 1/686

* cited by examiner

*Primary Examiner* — Jezia Riley

(57) ABSTRACT

This invention provides for processes for creating a long DNA molecule that is a concatamer that comprises a repeating oligonucleotide segment, wherein one or more of the nucleotides of said segment has one or more independently selected templating "non-standard" nucleotides. These are nucleotide analogs that, when incorporated into oligonucleotides (DNA or RNA, collectively xNA), present to a pattern of hydrogen bonds that is different from the pattern presented by adenine, guanine, cytosine, and uracil. This disclosure provides a process for obtaining these using rolling circle amplification.

6 Claims, 8 Drawing Sheets

Specification includes a Sequence Listing.

SEQUENCE LISTING

<160> NUMBER OF SEQ ID NOS: 2

<210> SEQ ID NO 1
<211> LENGTH: 66
<212> TYPE: DNA

```
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(49)
<223> OTHER INFORMATION: A, T, C, G,
      2-amino-8-(1'-beta-D-2'-deoxyribofuranosyl)-imidazo[1,2-a]-1,3,5-
      triazin-4(8H)one, or 6-amino-5-nitro-3-(1'-
      beta-D-2'-deoxyribofuranosyl)-2(1H)-pyridone

<400> SEQUENCE: 1
ctagcaacca gcacgaagcn nnnnnnnnnn nnnnnnnnnn nnnnnnnnna caggagcagg      60
tcgtgt                                                                66

<210> SEQ ID NO 2
<211> LENGTH: 18
<212> TYPE: DNA
<213> ORGANISM: Artificial Sequence
<220> FEATURE:
<223> OTHER INFORMATION: synthetic

<400> SEQUENCE: 2
gacacgacct gctcctgt                                                   18
```

BINDING MOLECULES BUILT FROM L-DNA WITH ADDED NUCLEOTIDES

CROSS REFERENCE TO RELATED APPLICATIONS

This application is a continuation-in-part of the currently pending U.S. patent application Ser. No. 15/639,336, filed 30 Jun. 2017, for "Binding and Catalytic Molecules Built from L-DNA with Added Nucleotides", which is a continuation-in-part of the U.S. patent application Ser. No. 14/082,800, filed 18 Nov. 2013 for "In vitro selection with expanded genetic alphabets", now U.S. Pat. No. 9,725,713, which is a continuation-in-part of the U.S. patent application Ser. No. 13/493,172, filed on Jun. 11, 2012 for In vitro selection with expanded genetic alphabets", now U.S. Pat. No. 8,586,303, which is a continuation-in-part of the U.S. patent application Ser. No. 12/999,138, filed Dec. 15, 2010 for "Polymerase incorporation of non-standard nucleotides", now U.S. Pat. No. 8,614,072. It claims the benefit of these parents.

STATEMENT OF RIGHTS TO INVENTIONS MADE UNDER FEDERALLY-SPONSORED RESEARCH

None

NAMES OF THE PARTIES TO A JOINT RESEARCH AGREEMENT

Not applicable.

INCORPORATION-BY-REFERENCE OF MATERIAL SUBMITTED ON A DISC

None.

BACKGROUND OF THE INVENTION

(1) Field of Invention

This invention relates to the field of nucleic acid chemistry, more specifically to nucleotide analogs, and still more specifically to "non-standard" nucleotide building blocks that, when incorporated into oligonucleotides (DNA or RNA, collectively xNA), present, to a complementary strand in a Watson-Crick pairing geometry, a pattern of hydrogen bonds that is different from the pattern presented by adenine, guanine, cytosine, and uracil. Further, this invention relates to functional nucleic acid analogs that fold in a way that allows them to bind to target molecules by mechanisms other than Watson-Crick hybridization. These are often called aptamers. Most specifically, this invention concerns processes for creating such functional nucleic acid analogs.

(2) Description of Related Art

For two decades, many have sought processes that mimic, in the laboratory, biological evolution to select or evolve DNA or RNA (collectively xNA) molecules that bind to non-nucleic acid partners, herein called "ligands". This process has been called Systematic Evolution of Ligands by Exponential Enrichment (SELEX), "in vitro selection", in vitro evolution, or "laboratory in vitro evolution" (hereinafter LIVE). These processes are collectively referred to here as LIVE. The xNA ligands and receptors that bind to a preselected target are often called aptamers.

The literature describing the history of development of LIVE is summarized in the U.S. patent application having Ser. Nos. 13/493,172 and 14/082,800, which rely on technology disclosed in the U.S. patent application having Ser. No. 12/999,138. All of these patent applications (collectively called "parents") are incorporated in their entireties by reference, including their drawings, abstract, and disclosures, including examples.

As generally practiced, LIVE generates aptamers or aptazymes by the following steps:

(a) A library of nucleic acid (xNA) molecules (typically $10^{14}$ to $10^{14}$ different species) is obtained.

(b) The library is then fractionated to create a fraction that contains molecules better able bind to the preselected target(s) than molecules in the fractions left behind. For example, to generate aptamers, this separation can be done by contacting the library with a solid support carrying the target, washing from the support xNA molecules that do not bind, and recovering from the support xNA molecules that have bound. xNA molecules within the library that bind to the target are said to survive the selection.

(c) The surviving xNAs are then used as templates for the polymerase chain reaction (PCR) process. A low level of mutation may be included in the PCR amplification, creating Darwinian "variation" in an in vitro evolution process.

(d) While aptamers/aptazymes having useful binding activity may emerge in the first "round" of selection, they generally do not. When they do not, the cycle is repeated. With each cycle of fractionation/selection and PCR amplification, the resulting fraction of xNA molecules becomes more enriched in those that bind to the preselected target.

(e) The product xNA aptamer(s) might be useful if their sequences are not known. However, the utility of these products is often enhanced if their sequences are known, as this allows them to be synthesized separately. To obtain those sequences, standard LIVE procedures generally clone the xNA products in their DNA form (either directly for DNA products, or after conversion to a DNA sequence using reverse transcriptase for RNA products) followed by classical sequencing. Alternatively, next generation sequence can be applied to the mixture of survivors. The elements of this approach are reviewed in U.S. Ser. Nos. 13/493,172 and 14/082,800.

U.S. Ser. Nos. 13/493,172 and 14/082,800 also review the many attempts to improve LIVE with functionalized natural DNA and RNA. However, simply functionalizing standard xNA nucleotides (as in SOMAmers) does not greatly expand its diversity of folds. Nor does it increase the information density of the biopolymer. Further, functionalizing GACT encounters a new set of problems. For example, an xNA molecule having a fluorescent group attached to each nucleobase are hard to make using xNA polymerases. Further, in ways that are not fully understood, having each nucleobase carry a functional group can cause the DNA to cease to follow "rule based" molecular recognition essential for its genetic roles.

U.S. Ser. No. 13/493,172 also discussed how many of the disadvantages of standard LIVE aptamers and aptazymes might be mitigated by expanding the number of nucleotides in DNA. For example, rearranging hydrogen bond donor and acceptor groups on the nucleobases increases the number of independently replicable nucleosides in DNA and RNA from four to twelve (FIG. 1 and FIG. 2). In this "artificially expanded genetic information system" (AEGIS), as many as 12 different nucleotide "letters" pair via as many as six distinguishable hydrogen bonding patterns to give a system that can be copied and evolve like natural DNA, using processes disclosed in the parents. The products are oligonucleotides with higher information density and more functional group diversity than standard DNA or RNA (collectively xNA).

The potential for using AEGIS to support LIVE has been recognized since the proposal of the first AEGIS. Indeed, processes for doing LIVE with certain AEGIS-containing nucleotides were offered by U.S. Pat. No. 5,965,363. However, the processes disclosed in that patent failed to work. Steps (a) and (b) (above) in the LIVE process were possible. Libraries of xNA molecules containing AEGIS components could be prepared, Step (a), and these libraries could be fractionated (Step (b)). However, as disclosed in U.S. Ser. No. 13/493,172, polymerases were not available to perform PCR on DNA molecules containing multiple AEGIS nucleotides.

BRIEF SUMMARY OF THE INVENTION

The parents cover and claim processes for creating aptamers that incorporate AEGIS. Two issues are addressed in the instant application to further increase the utility of these products. The first recognizes that the more AEGIS components one has in such products, the better they generally perform. Even with the improved polymerases described in the parents, AEGIS components are often lost in the PCR amplification process that occurs in standard LIVE in between selection steps. This is because in PCR, a majority of the products come from copying the copies of the copies, and so on. In each copying step, an opportunity exists for information to be lost, just as repeated Xerox copying of a Xerox of a copy of a Xerox copy will lead to low information.

The second advance relates to the desire to use AEGIS aptamers and aptazymes in complex biological media that contain enzymes that bind and digest xNA. These enzymes are known, however, to act only on xNA molecules that are built from nucleosides where the ribose or 2'-deoxyribose has a "D-configuration"; this corresponds to a 4'-R absolute configuration. However, the AEGIS-containing aptamers and aptazymes are not digested by nucleases where the ribose or 2'-deoxyribose has the mirror image "L-configuration"; this corresponds to a 4'-S absolute configuration. This is well known in fully standard xNA molecules that do not contain AEGIS components [Eulberg, D., Klussmann, S. (2003). Spiegelmers. Biostable aptamers. *Chembiochem* 4, 979-983]. However, Hitherto, No Oligonucleotides Containing Non-Standard nucleotides built from L-nucleosides have been reported. This invention provides xNA analogs containing non-standard nucleobases attached to L-nucleosides.

Most specifically in its presently preferred embodiments, this invention concerns the use, as aptamers and aptazymes, of AEGIS-containing oligonucleotide analogs where the AEGIS components are, without limitation:

2-amino-8-(1'-β-D-2'-deoxyribofuranosyl)-imidazo[1,2-a]-1,3,5-triazin-4(8H)one (trivially called D-dP where the initial "D" indicates the stereochemical configuration of the ribose, and "d" indicates that the species is the 2'-deoxynucleoside), 2-amino-8-(1'-β-L-2'-deoxyribofuranosyl)-imidazo[1,2-a]-1,3,5-triazin-4(8H)one (trivially called L-dP where the initial "L" indicates the stereochemical configuration of the ribose, and "d" indicates that the species is the 2'-deoxynucleoside), 6-amino-5-nitro-3-(1'-β-D-2'-deoxyribofuranosyl)-2(1H)-pyridone (trivially called D-dZ), 6-amino-5-nitro-3-(1'-β-L-2'-deoxyribofuranosyl)-2(1H)-pyridone (trivially called L-dZ), 4-Amino-7-[2'-deoxy-5-beta-D-erythropentofuranosyl]1,7-dihydro-2H-pyrrolo[2, 3-d]-pyrimidin-2-one (trivially called D-dB, or 7-deazaisoguanosine), and isocytosine heterocycles.

4-Amino-7-[2'-deoxy-5-beta-L-erythropentofuranosyl]1,7-dihydro-2H-pyrrolo[2, 3-d]-pyrimidin-2-one (trivially called L-dB, or 7-deazaisoguanosine), and isocytosine heterocycles.

2-amino-5-methyl-1-(1'-beta-D-2'-deoxyribofuranosyl)-4(1H)-pyrimidinone, (trivially called D-dS, or isocytidine) and/or 2-amino-5-methyl-1-(1'-beta-L-2'-deoxyribofuranosyl)-4(1H)-pyrimidinone, (trivially called L-dS, or isocytidine)

BRIEF DESCRIPTION OF THE DRAWINGS

FIG. 7. Polyacrylamide gel electrophoresis (PAGE) analysis of results of treating a library of oligonucleotides built from a six letter genetic alphabet, with a random region of 30 nucleotides embedded within two primer sections as shown in SEQ ID 1, with Circligase™ (Lucigen). The circuligation is indicated by a band running similar to a single-stranded oligonucleotide 120 nucleotides long (Lane 2). The uncircularized starting material can be removed by exonuclease 1 (Lane 3). The linear material is shown in Lanes 4 and 5. The sequence of the library is: 5' CTA GCA ACC AGC ACG AAG C (N)$_{30}$ ACA GGA GCA GGT CGT GT3', which is equivalent to:

SEQ ID 1
CTAGCAACCAGCACGAAGC NNNNNNNNNN NNNNNNNNNN

NNNNNNNNNN ACAGGAGCAGGTCGTGT

Figure 8:
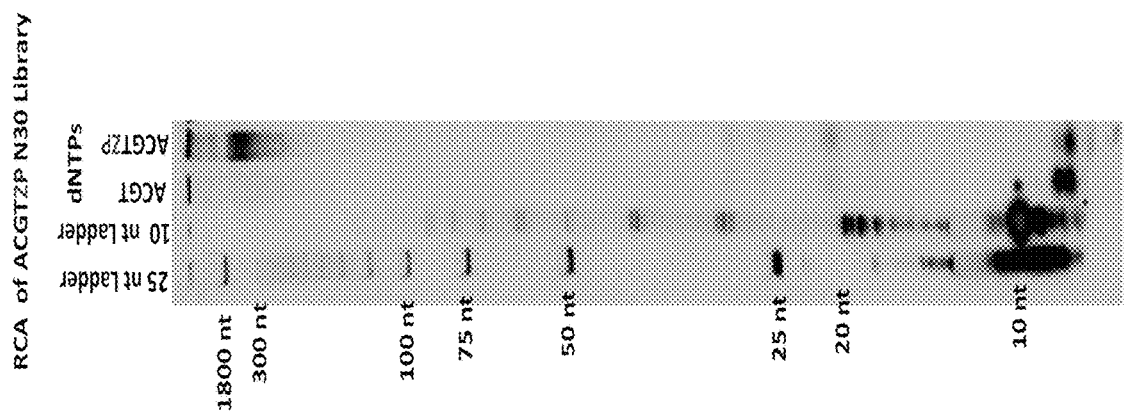

FIG. 8. PAGE analysis of the results of amplification of the circularized product obtained using Circligase™ in a Phi 29/Phi 29 polymerase/buffer system including either a standard (A/C/G/T) or AEGIS containing (A/C/G/T/Z/P) dNTP mix using polyacrylamide gel electrophoresis (PAGE) with α-[$^{32}$P] GTP. With just four standard triphosphates, product (the broad band between 300 and 1800 nts) is not seen. RCA products are sonicated before PAGE. ACGTZP N30 library (CN30).

DESCRIPTION OF INVENTION

Definition of Non-Standard Components of an Artificially Expanded Genetic Information System This application teaches a distinction between the hydrogen-bonding pattern (in FIG. 1 and FIG. 2 nomenclature, pyDAD, for example) and the heterocycle that implements it. Thus, the pyADA hydrogen-bonding pattern is implemented by thymidine, uridine, and pseudouridine. The puDDA hydrogen bonding pattern is implemented by both the heterocycle isoguanosine and 7-deaz-isoguanosine. Heterocycles to implement any particular pre-selected hydrogen-bonding pattern are preferred depending on their chemical properties, for example, high chemical stability or low tautomeric ambiguity. The pyADA, pyDAA, puADD, and puDAD hydrogen bonding patterns are said to be "standard" hydrogen bonding patterns, and to form with their appropriate complement "standard base pairs". Other hydrogen bonding patterns are said to be "non-standard", and to form with their appropriate complement "non-standard base pairs".

Creating AEGIS-Containing Oligonucleotides Having all of the Carbohydrate Suitors in the L-Configuration The strategy to generate binding and reactive AEGIS sequences that are stable in cancer-relevant biological environments relies in our ability to present them in their mirror-image form, These in AEGIS-free oligonucleotides are not be substrates for any natural nucleases, including those found in human blood and tissues; mirror image xNA is stable in blood, for example, for as long as 72 hours [Kim, K. R., Lee, T., Kim, B. S., & Ahn, D. R. (2014). Utilizing the bioorthogonal base-pairing system of L-DNA to design ideal DNA nanocarriers for enhanced delivery of nucleic acid cargos. Chem. Sci. 5, 1533-1537.].

Synthesis of L-AEGIS oligonucleotides is implemented using solid phase phosphoramidite chemistry, well known in the art. The only difference is that the phosphoramidite building blocks have the L configuration, and are prepared by one of the processes described in the drawings.

The sequence for the L-AEGIS oligonucleotide(s) that bind and/or chemically transform to an achiral target is obtained simply by following the processes disclosed in the parents. Since the target is not chiral, the L-AEGIS oligonucleotide will bind to and/or chemically transform that achiral target with exactly the same affinity and/or exactly the same rate as the D-AEGIS oligonucleotide.

The sequence for the L-AEGIS oligonucleotide(s) that bind and/or chemically transform to a chiral target is obtained by following the processes disclosed in the parents, except by using the target in its mirror image enantiomeric form. The processes disclosed in the parents will generate D-AEGIS oligonucleotide(s) that bind to and/or chemically transform that chiral target in the form that is the mirror image of the desired target, Then, by symmetry laws in physics, the L-AEGIS oligonucleotide will bind to and/or chemically transform the chiral target in the desired enantiomeric form with exactly the same affinity and/or exactly the same rate as the D-AEGIS oligonucleotide binds to and/or transforms the target in its mirror image enantiomeric form.

When the desired target is a natural translated protein, which is built from L-amino acids, the target must be the same protein sequence, except built from D-amino acids, Kent and his colleagues have used convergent synthesis to make mirror-image proteins that are arbitrarily large [Kent, S. B. (2009). Total chemical synthesis of proteins. Chemical Society Reviews 38, 338-351]. Alternatively, AEGIS-LIVE may be targeted against a surface loop peptide of a target protein, preferably a flexible surface loop peptide, in the target protein, but synthetic so that it is built from D-amino acids [Rowlands, D. J., Clarke, B. E., Carroll, A. R., Brown, F., Nicholson, B. H., Bittle, J. L., Houghten, R. A. & Lerner, R. A. (1983) Nature (London) 306, 694-697.][Alexander, H., Johnson, D. A., Rosen, J., Jerabek, L., Green, N., Weissman, I. L. & Lerner, R. A. (1983) Nature (London) 306, 697-699.] [Geysen, H. M., Barteling, S. J., & Meloen, R. H. (1985). Small peptides induce antibodies with a sequence and structural requirement for binding antigen comparable to antibodies raised against the native protein. Proc. Natl. Acad. Sci. USA 82, 178-182.]. This presently preferred process follows rules to how to extract peptides from a full protein to serve for this purpose [Walter, G. (1986). Production and use of antibodies against synthetic peptides. J. Immunol. Meth. 88, 149-161.

To force the peptide to adopt a turn conformation, the presently preferred implementation places cysteines at the end of the peptide. These form a cyclic disulfide is conformation resembles that of the natural were turned in a natural protein. Again, the amino acids must have the D-configuration.

The currently claimed method for implementing this involves a rolling circle amplification, or RCA. Here, a circular oligonucleotide is created from linear nucleotide in any of a number of ways. This includes a ligation exploits of splint. It also includes using an enzyme called Circligase™, which does not require a splint. The presently preferred circular oligonucleotides are between 50 and 200 nucleotides in length. They embody a segment that contains one or more nonstandard nucleotides, specifically preferred or those shown in FIG. 1. The most preferred of those in that figure are designated P and Z in the literature.

Once circularized, a strand displacing DNA polymerase can extend a primer that is annealed to the circle. This requires the appropriate buffer, temperature, and salt concentrations, as well as nucleoside triphosphates. This primer extension generates what is known as a concatamer. This concatamer is a long oligonucleotide that contains repeating segments that are complementary to the sequence of the DNA circle that is acting as a template. For successful concatamer formation, all the triphosphates must be present, that is, each and every nucleotide in the templating DNA circle must find in the solution the triphosphate of the complementary nucleoside. For example, if the circularized DNA template contains a dP, then the RCA requires the mixture to contain the complementary dZTP. Likewise, if the circularized DNA template contains a dZ, then the RCA requires the mixture to contain the complementary dPTP. Presently preferred are templates that contain dZ and dP, meaning that the presently preferred triphosphate mixtures contain dPTP and dZTP. Also likewise, the standard triphosphates must be present in the RCA incubation mixture as necessary to complement the standard templating nucleotides in the circular template.

EXAMPLES

Example 1. Synthesis of a Glycal Having the Unnatural L-Configuration

Figure 3:
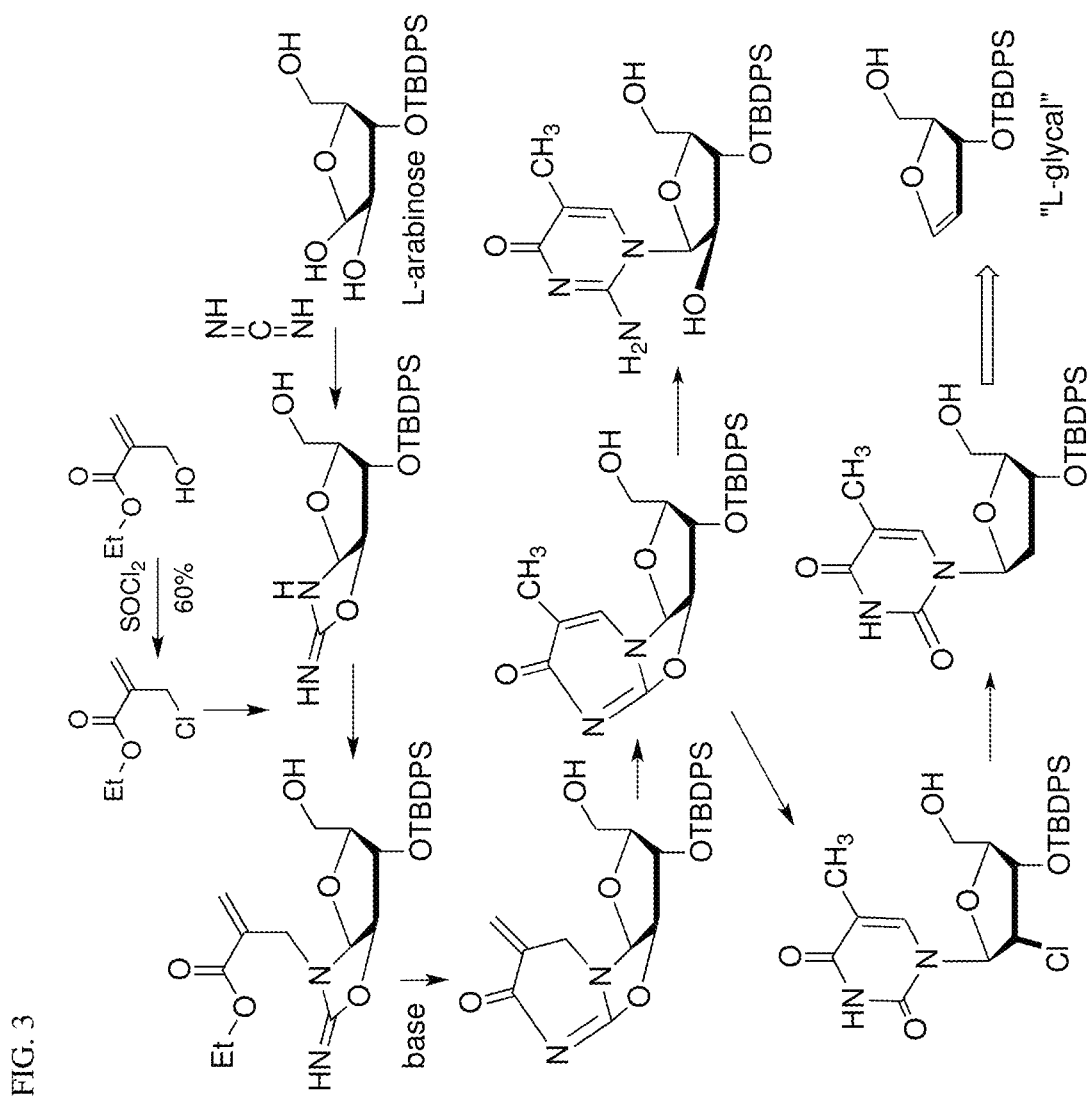
FIG. 3. Synthetic route generates a glycal having the L-configuration. This is a precursor for synthesizing all C-glycosides in the instant invention, specifically from FIG. 1, the heterocycles implementing the V, K, and Z hydrogen bonding patterns, and in FIG. 2, the heterocycles implementing the S, V, K, and Z hydrogen bonding patterns following routes covered in the parents of the instant application. This drawing also described the route to prepare the FIG. 1 AEGIS S in its epimeric form.

The mirror image L-nucleotides for G, A, T, and C needed to construct the L-AEGISbodies are commercially available. However, the L-AEGIS nucleotides that are used to synthesize the L-AEGISbodies are not. The precursor for the AEGIS components that are C-glycosides is prepared by the literature route shown in FIG. 3. Arabinose, a very inexpensive L-sugar, is the precursor. The same route, adapted from the parents for the L-glycal, leads to the formation of RNA AEGIS building blocks.

Example 2. Synthesis of a L-AEGIS Nucleoside Phosphoramidites Suitable for Solid Phase DNA Synthesis, Here Implementing the Z Hydrogen Bonding Pattern from FIG. 2

Figure 4:
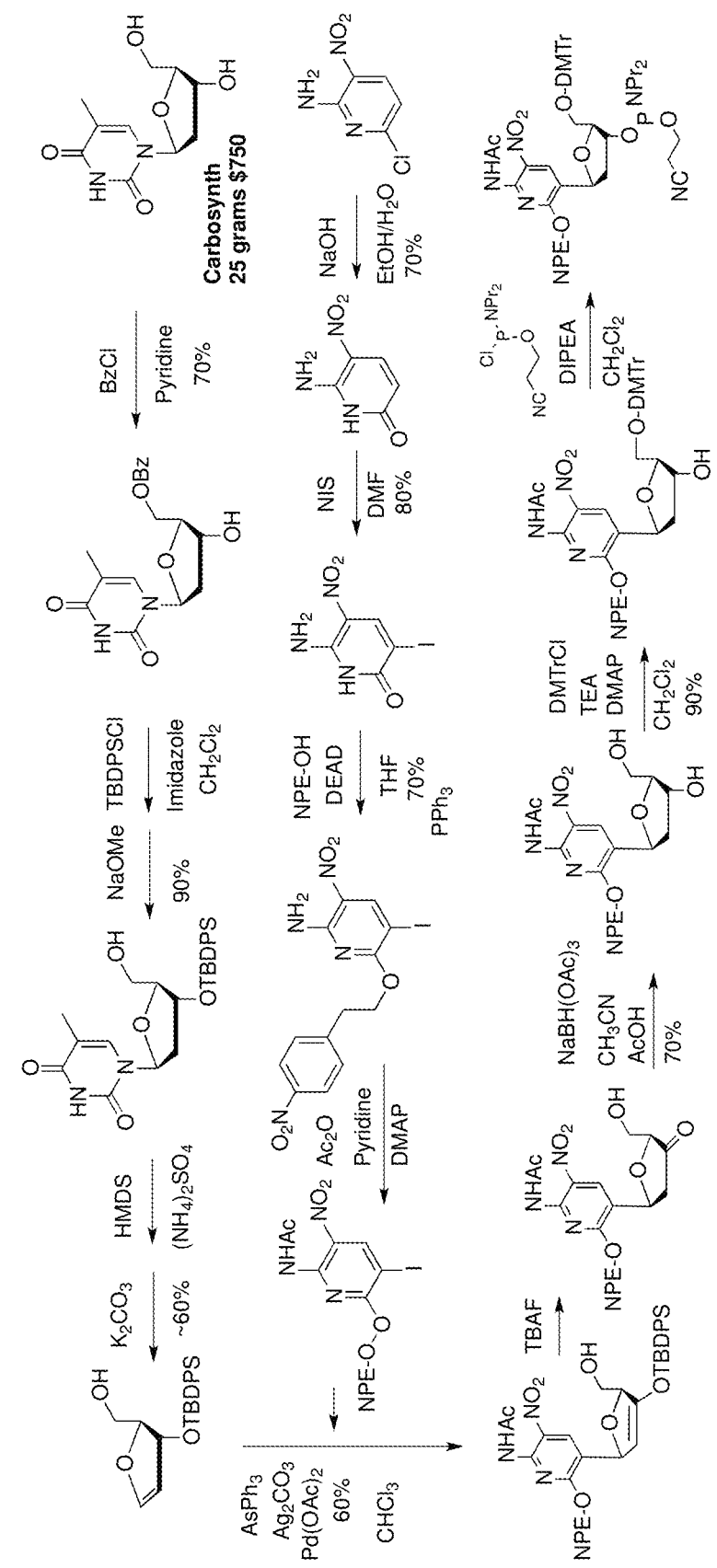
FIG. 4. Synthetic route to a protected phosphoramidite of AEGIS Z follows routes that are described in the parents. The precursor is commercially available from Carbosynth.
Figure 5:
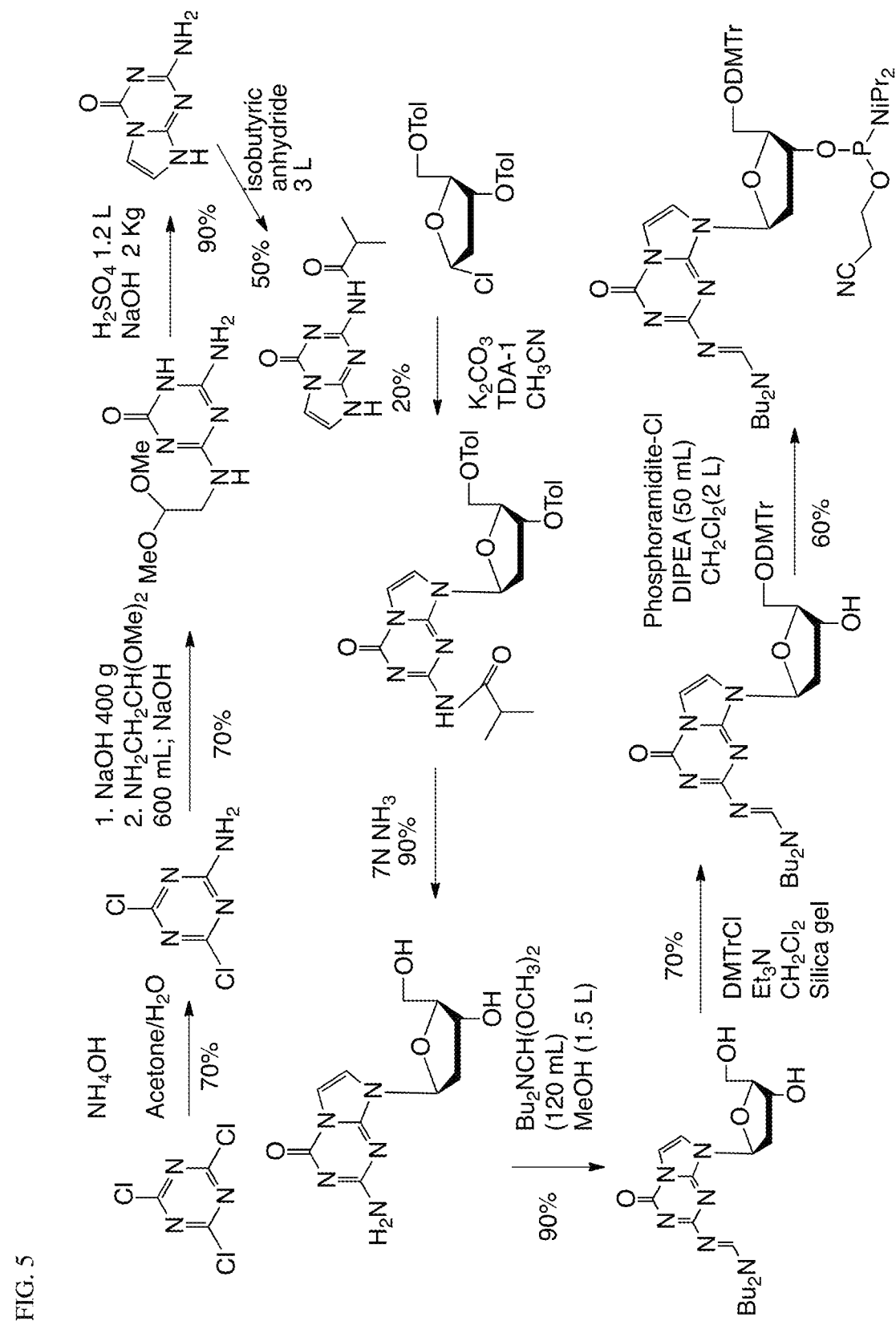
FIG. 5. Synthetic route to generate L-AEGIS P. Other AEGIS N-glycoside analogs are prepared analogously following routes described for the D-enantiomer in the parents.
Figure 6:
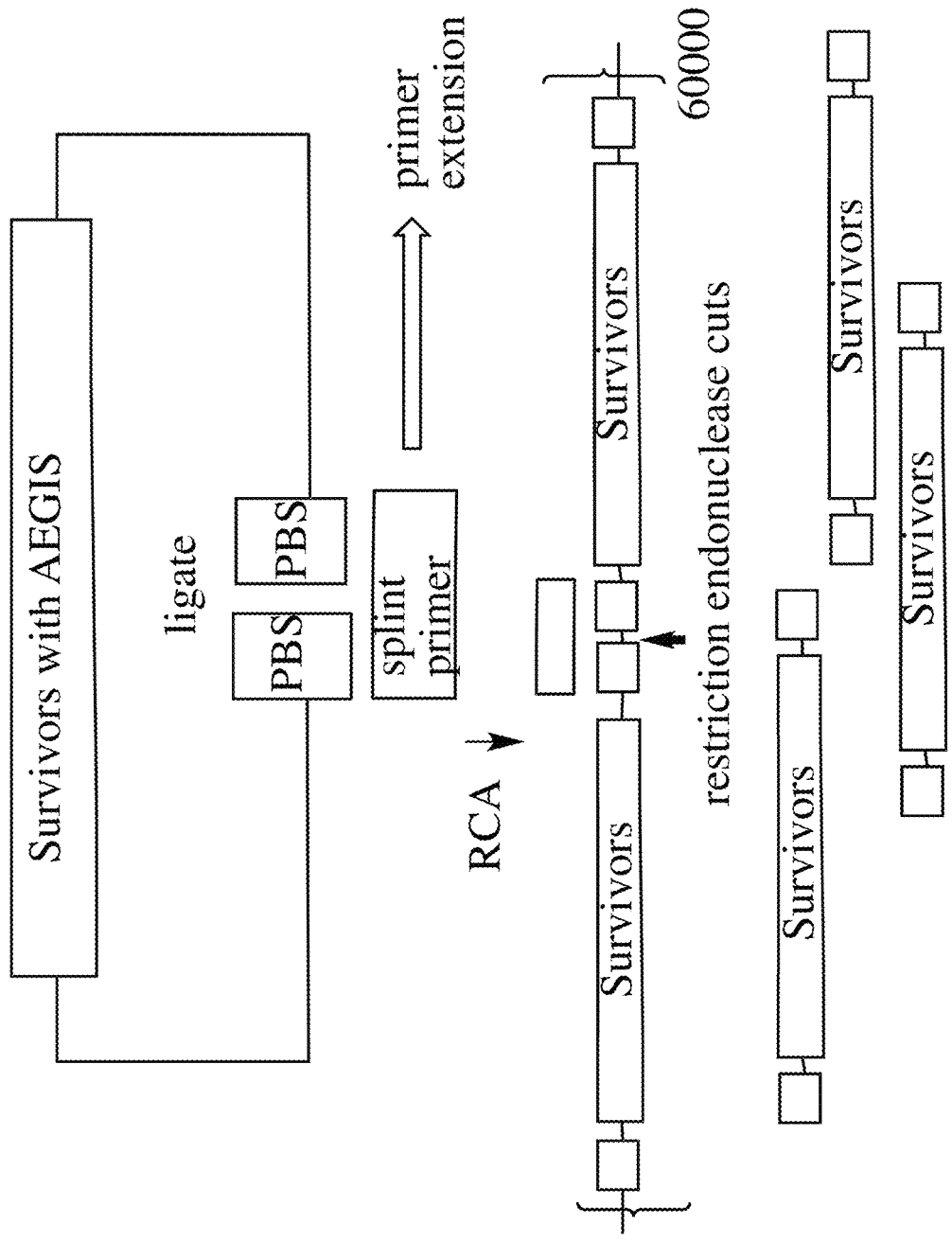
FIG. 6. Rolling circle amplification (RCA) is disclosing this diagram as an alternative to PCR way to amplify survivors from an AEGIS-LIVE, the process disclosed in the parents. Here, instead of the primer binding sites (PBS) being used to bind primers in the PCR, those same sites are used to anneal to a splint which allows the ligation of the survivors to form a circle. The splint can then be used as a primer for rolling circle amplification, leading to between 10,000 and 100,000 copies of the survivor sequence(s) as a linear concatamer. These can then be cleaved by a restriction enzyme placed strategically to yield the same number of short survivor sequence(s) which can be introduced into AEGIS-LIVE. The presently preferred polymerase for the RCA is the Phi 29 polymerase, which is commercially available, Bst I or other strand displacing polymerase.

An alternative route to C-glycosidic AEGIS components that are C-glycosides is shown in FIG. 4. This alternative route starts from L-thymidine, which is presently available from Carbosynth for $750/25 grams. This also follows synthetic procedures disclose in the parents. The inversion of configuration does not change any of the chemistry involved.

Example 3. Synthesis of a L-AEGIS Nucleoside Phosphoramidites Suited for Solid Phase DNA Synthesis, Implementing the P Hydrogen Bonding Pattern from FIG. 1 and FIG. 2

The route to prepare N-glycosidic AEGIS components in a protected form. This starts with the-L chlorosugar. Again, this follows synthetic procedures disclose in the parents. The inversion of configuration does not change any of the chemistry involved.

Example 4. Preparing the Circularized Library

As unpredictable arts, chemistry and biochemistry require experimental validation to establish without undue experimentation that an enzyme that can be used to create circular libraries of standard DNA nucleotides actually works when the oligonucleotides being circularized contain nonstandard nucleotides, and that enzymes capable of doing rolling circle amplification (RCA) with standard nucleotides can indeed copy DNA containing nonstandard nucleotides.

Figure 1:
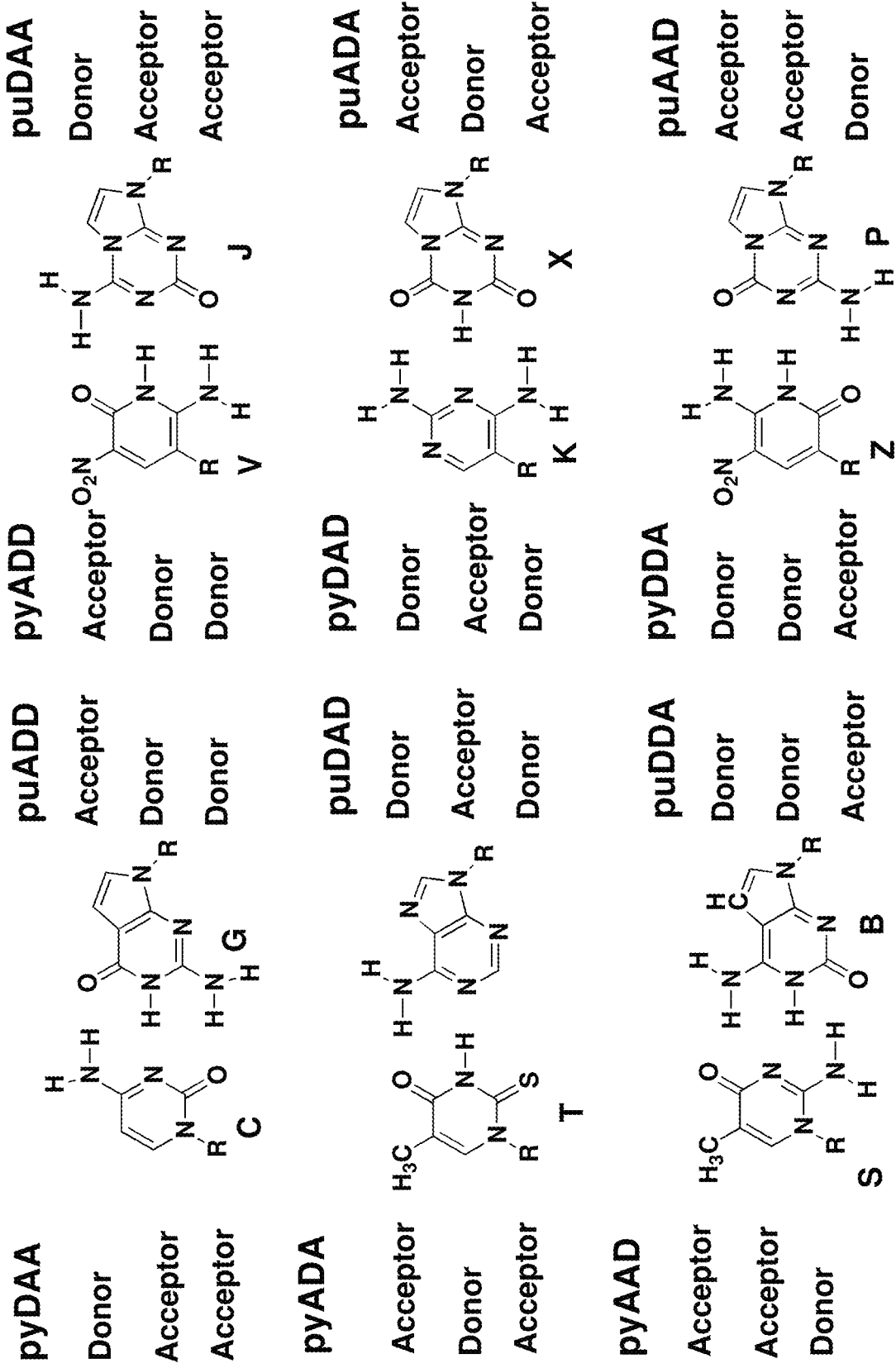
FIG. 1. Watson-Crick pairing rules follow two rules of complementarity: (a) size complementarity (large purines pair with small pyrimidines) and (b) hydrogen bonding complementarity (hydrogen bond donors, D, pair with hydrogen bond acceptors A). Rearranging D and A groups on various heterocycles supports an artificially expanded genetic information system (AEGIS). These are the presently most preferred heterocycles for the instant invention. The nucleotides herein that are not found in natural DNA or RNA are called "non-standard".
Figure 2:
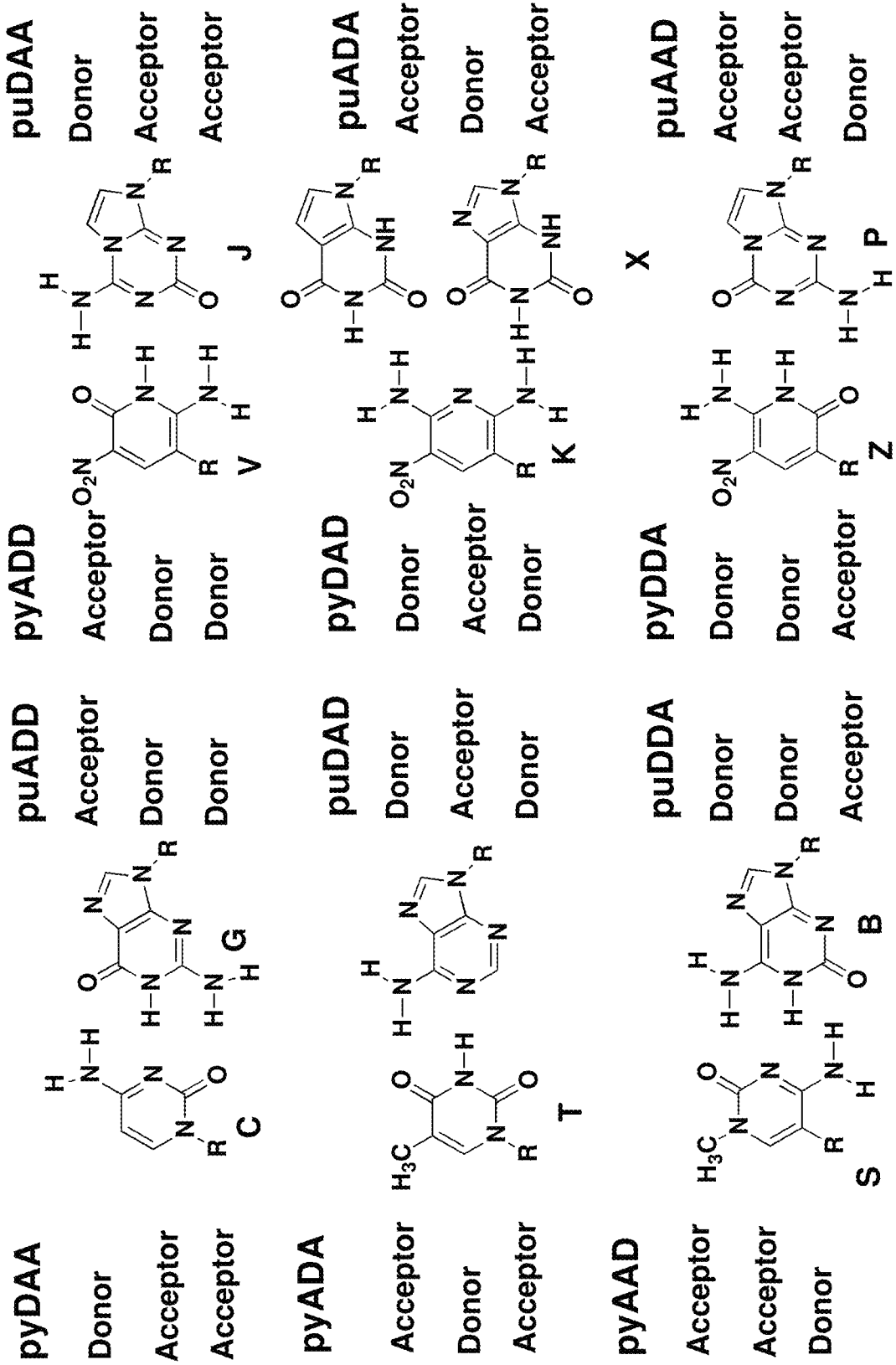
FIG. 2. This invention teaches the different heterocycles can implement the same hydrogen bonding pattern. Shown here are presently preferred heterocycles for implementing the instant invention, as alternatives. The nucleotides herein that are not found in natural DNA or RNA are called "non-standard".

In this example, we discover unexpectedly that this is the case with both dP and dZ (FIG. 1). This example compares RCA amplification of a circularized "ACGTZP N30" library using the strand displacing Phi 29 DNA polymerase in aPhi 29 DNA polymerase reaction buffer system.

Figure 7:
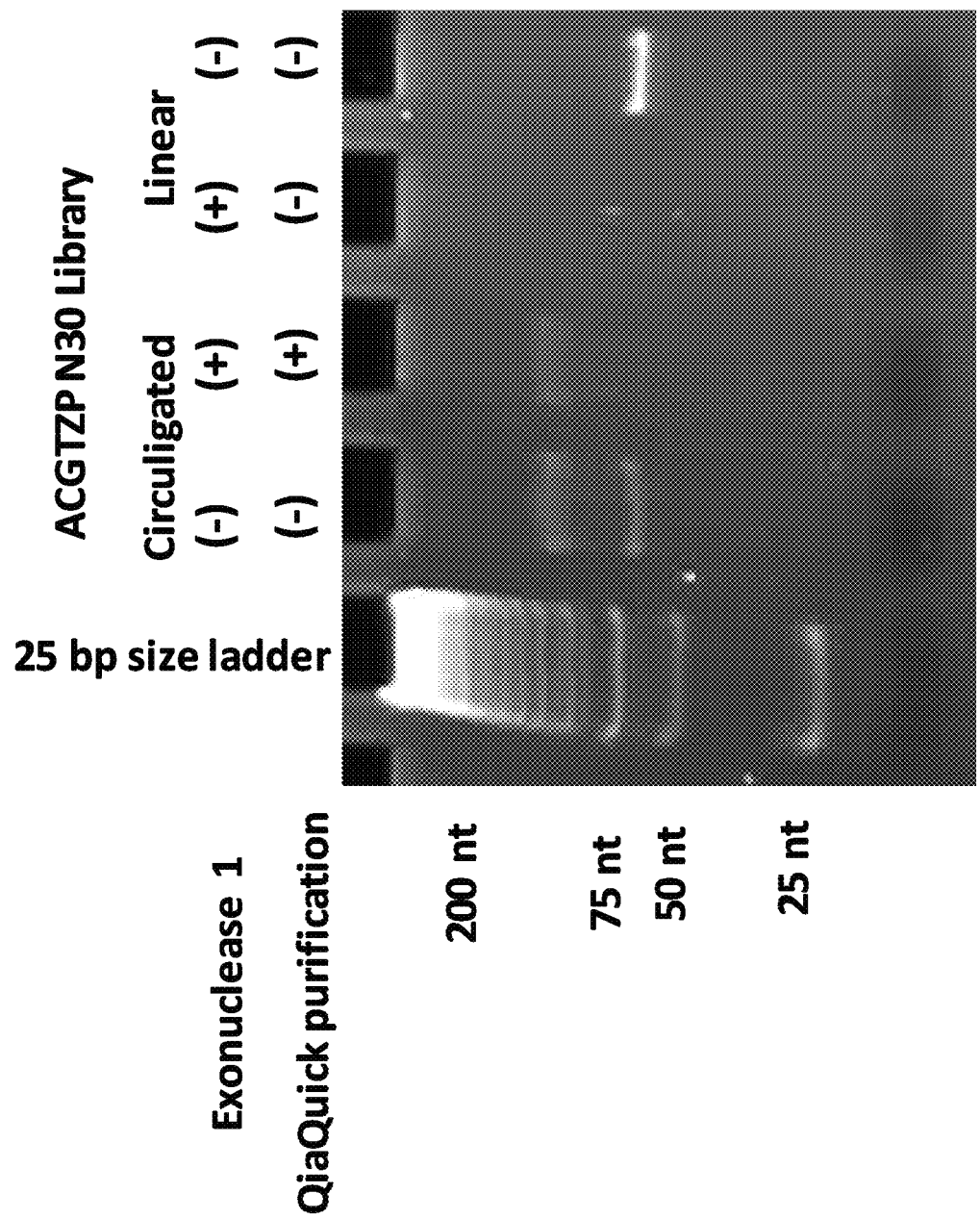

Here, SEQ ID 1 (Molar Extinction Coefficient: $1.63 \times 10^{-7}$) was treated with Circligase™ (Lucigen) under conditions recommended by the manufacturer. The products were then analyzed by PAGE. Successful circuligation is indicated by a band running similar to a single-stranded oligonucleotide 120 nucleotides long (Lane 2, FIG. 7). The unciruclized starting material can be removed by exonuclease 1 (Lane 3). The linear material is shown in Lanes 4 and 5.

This material was then contacted with a primer in a RCA reaction mixture:

5'-GACACGACCTGCTCCTGT-3' SEQ ID 2

RCA reaction mixtures (20 µL) contained the following: 0.07 µM purified circularized ACGTZP N30 Library (CN30) (from SEQ ID 1), 1 µM of primer (SEQ ID 2), 1× of Phi 29 reaction buffer (50 mM Tris HCL, 10 mM $(NH_4)_2SO_4$, 10 mM $MgCl_2$, and 4 mM DTT at, pH 7.5), 0.125 µM BSA, dNTP mix (either dA/dC/dT or dA/dC/dT/dZ/dP at 1 mM combined with unlabeled dGTP at 0.7 mM and 0.01 µM $^{32}P$ alpha dGTP), 0.4 U/µL of the Phi 29 polymerase and water (q.s.).

For each sample, a 10 µL solution of template, primer and 1× reaction buffer is heated to 85° C. for 1 minute and cooled to R°T to anneal primer to template.

Ten microliters of a reaction mix containing the Phi 29 polymerase/reaction buffer along with cold dNTPs, $^{32}P$ alpha dGTP and water (q.s.) were added to each cooled annealed primer/template sample. Samples were incubated for 2 hours at 30° C.

Following incubation the 20 µL RCA reaction mixtures were diluted to 1 to 2 with water (40 µL total). The diluted RCA products were sonicated at room temperature with 3×10 second bursts with a 10 second interval between. Upon sonication, the high molecular weight CN30 RCA product (1800 nt to approximately 200 nt).

The noted feature of the gel shown in FIG. 8 is that RCA product is seen when all six triphosphates were presented (dATP, dCTP, dGTP, TTP, dZTP, dPTP), while no RCA product is detectable when dZTP and dPTP are absent. This feature is quantitated by densitometry measurements of the RCA product (top "smear") versus the free $^{32}P$ alpha dGTP (bottom band) as the radiolabel incorporation percentages are 32% versus 84% with standard and the dZTP, dPTP containing dNTP mixes, respectively. These results indicate that the presence of Z and P greatly enhances the amount of RCA product, and, in turn, leads to the conclusion that Phi 29 polymerase is able to incorporate both dZ and dP into a concatamer product under these conditions. It further drives the conclusion that in substantial amounts of dZ and dP are lost through mismatches of template dZ and dP should dZTP and dPTP be absent.

What is claimed is:

1. A process to create an oligonucleotide concatamer, said concatamer comprising a repeating oligonucleotide segment, wherein at least one of the nucleotides of said segment has a templating nucleobase selected from the group consisting of

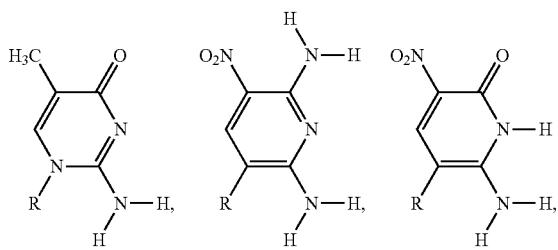

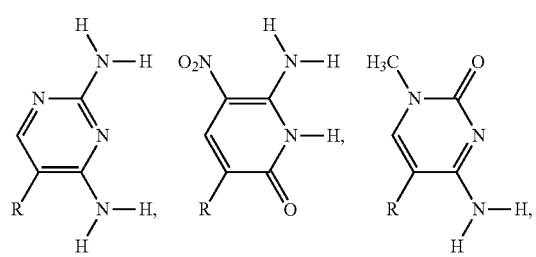

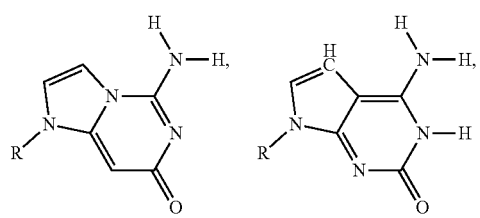

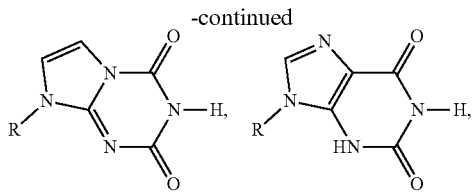

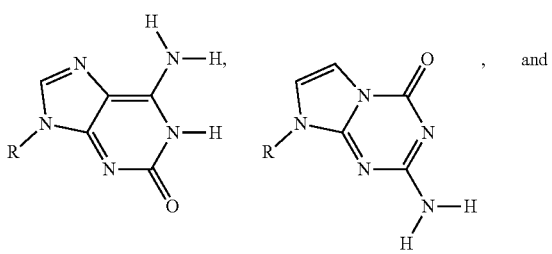

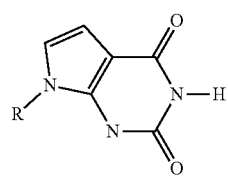

wherein R is the point of attachment of said templating nucleobase to said oligonucleotide segment, wherein said process comprises contacting a circular oligonucleotide that comprises a segment that is Watson-Crick complementary to said repeating oligonucleotide segment with (i) a primer, (ii) a strand displacing polymerase, and (iii) a group of nucleoside triphosphates, wherein said nucleobases of said group complement all of the nucleobases in said circular oligonucleotide.

2. The process of claim 1, wherein said strand displacing polymerase is the phi 29 DNA polymerase.

3. The process of claim 1, wherein said nucleobase is

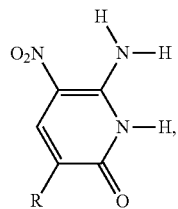

where R is the point of attachment of said nucleobase to said oligonucleotide.

4. The process of claim 1, wherein said nucleobase is

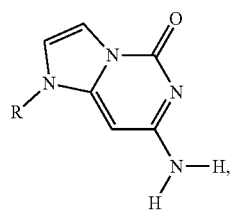

where R is the point of attachment of said nucleobase to said oligonucleotide.

5. The process of claim 1, wherein said nucleobase is

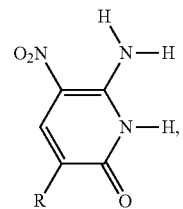

where R is the point of attachment of said nucleobase to said oligonucleotide.

6. The process of claim 1, wherein said nucleobase is

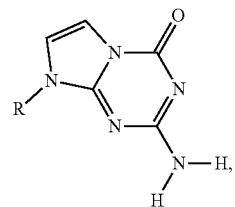

where R is the point of attachment of said nucleobase to said oligonucleotide.

* * * * *